United States Patent [19]

Rauleder et al.

[11] Patent Number: 5,786,493
[45] Date of Patent: Jul. 28, 1998

[54] CYCLIC SILANE ESTERS AND SOLVOLYSIS PRODUCTS THEREOF, AND PROCESSES FOR THE PREPARATION OF THE CYCLIC SILANE ESTERS AND THE SOLVOLYSIS PRODUCTS

[75] Inventors: Hartwig Rauleder; Hans-Joachim Koetzsch; Jaroslaw Monkiewicz; Claus-Dietrich Seiler, all of Rheinfelden; Hans-Guenther Srebny, Nienburg, all of Germany

[73] Assignee: Huels Aktiengesellschaft, Marl, Germany

[21] Appl. No.: 895,477

[22] Filed: Jul. 16, 1997

[30] Foreign Application Priority Data

Jul. 16, 1996 [DE] Germany ............ 196 28 588.7

[51] Int. Cl.$^6$ ............................................. C07F 7/08
[52] U.S. Cl. ............ 556/443; 556/444; 556/464; 106/273.1; 428/571; 428/551; 428/402; 428/405; 428/423.1; 428/466; 428/425.5; 428/430; 428/450; 428/447; 428/693; 521/155; 528/28; 528/29
[58] Field of Search ............... 556/443, 444, 556/464; 106/273.1; 428/571, 562, 402, 405, 423.1, 466, 425.5, 430, 450, 447, 693; 521/155; 528/28, 29

[56] References Cited

U.S. PATENT DOCUMENTS

| | | | |
|---|---|---|---|
| 2,983,745 | 5/1961 | Speier | 556/464 |
| 3,218,271 | 11/1965 | Wong et al. | 556/443 |
| 3,535,610 | 10/1970 | Berger | 556/464 |

FOREIGN PATENT DOCUMENTS 991786  5/1965  United Kingdom.

OTHER PUBLICATIONS

John L. Speier, J. Am. Soc., vol. 74, pp. 1003–1010, Feb. 20, 1952, "The Preparation and Properties of (Hydroxyorgano)–Silanes and Related Compounds".

V. Chvalovsky, et al., Tetrahedron, vol. 39, No. 7, pp. 1195–1197, 1983, "7– and 8–Membered Oxasilacycloalkanes–I".

Primary Examiner—Paul F. Shaver
Attorney, Agent, or Firm—Oblon, Spivak, McClelland, Maier & Neustadt, P.C.

[57] ABSTRACT

Cyclic silane esters and solvolysis products thereof and processes for making these materials. The cyclic silanes and their solvolysis products are useful as adhesives, crosslinking agents and reagents for modifying polymers containing ester groups.

26 Claims, No Drawings

CYCLIC SILANE ESTERS AND SOLVOLYSIS PRODUCTS THEREOF, AND PROCESSES FOR THE PREPARATION OF THE CYCLIC SILANE ESTERS AND THE SOLVOLYSIS PRODUCTS

BACKGROUND OF THE INVENTION

1. Field of the Invention

The present invention is directed to cyclic organosilane esters, cyclic organyloxyorganosilane esters and solvolysis products thereof. The present invention is also directed to processes for preparing these compounds.

2. Description of the Background

EP-A-991 786 describes a process for preparing cyclic silane esters, in particular 1-sila-2-oxacyclopentane derivatives. For example, 1-methyl-1-ethoxy-1-sila-2-oxacyclopentane:

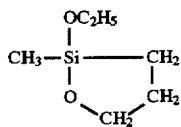

is prepared by intramolecular transesterification of 3-acetoxypropylmethyldiethoxysilane in ethanol and in the presence of sodium ethanolate. In this reaction, ethyl acetate is formed in equimolar amounts from the acetyl group which functions as a protecting group. This by-product contaminates the desired silane. Therefore, the ethyl acetate must be separated off from the reaction product. This is a disadvantage because removing the ethyl acetate requires an additional purification step. As a result, costs increase and the increased expenditure impedes the use of this process on an industrial scale.

A similar problem is encountered with the trimethylsiloxy group proposed as a protecting group by J. L. Speier (see J. Am. Soc. 74, 1003–1010 (1952)). According to V. Chvalovsky et al., Tetrahedron 39 (1983), 11 95–1197, alpha-trimethylsiloxy-omega-alkenes can be reacted with methylalkoxyhydridosilanes in a hydrosilylation reaction catalyzed by platinum compounds to produce open-chain adducts. These adducts can be subjected to intramolecular condensation with alcoholates in a subsequent step to give cyclic oxasilacycloalkanes having 7 or 8 ring members. In this reaction, a trimethyl-alkoxysilane is formed in equimolar amounts as an undesirable by-product which contaminates the process.

OBJECTS OF THE INVENTION

Accordingly, it is an object of the present invention to provide a process for preparing cyclic silane esters and solvolysis products thereof that does not produce contaminating by-products.

It is another object of the present invention to provide cyclic silane esters and solvolysis products thereof.

It is another object of the present invention to provide cyclic silane esters and solvolysis products thereof that contain polyglycol ether groups.

It is another object of the present invention to provide a composition containing silane esters or solvolysis products thereof.

SUMMARY OF THE INVENTION

The above objects and others are accomplished by a process for preparing a cyclic silane ester or a solvolysis product thereof, comprising:

(A) reacting a hydridosilane of the general formula I:

where X is a hydrolyzable radical, each $R^1$ is, independently, a hydrolyzable radical or $R^2$ and $R^3$ is an organic radical bonded by a carbon atom, with an allyl compound containing a hydroxyl group of formula II:

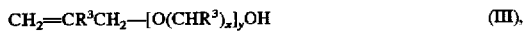

where $R^3$ is hydrogen or a methyl radical, x is an integer from 2 to 6 and y is 0 or an integer or fraction up to 60, in a condensation reaction to produce an open-chain, olefinically unsaturated organohydridosilane ester of formula III:

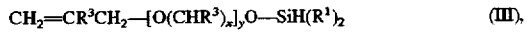

where $R^1$, $R^3$, x and y are as defined above; and (B) reacting the organohydridosilane ester of formula (III) in an intramolecular hydrosilylation reaction to produce a cyclic organosilane ester of formula IV:

(IV)

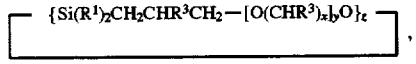

where $R^1$, $R^3$, x and y are as defined above and z is an integer from 1 to 6.

The above objects are also accomplished with a process comprising stages (A) and (B) above and further comprising:

(C) reacting the cyclic ester of formula IV with an alcohol having the formula $R^2OH$ to produce a cyclic organyloxyorganosilane ester of formula V:

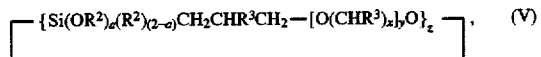

wherein at least one $R^1$ in formula IV is a halogen radical, $R^3$, x, y and z are as previously defined, each $R^2$ is, independently, as previously defined, and a is 1 or 2.

The above objects are also accomplished with a process comprising stages (A), (B) and (C) above and further comprising:

(D) solvolyzing the organyloxyorganosilane ester of formula V with either:

(1) water to produce a hydrolysis product of formula VI:

wherein $R^2$, $R^3$, a, x and y are as previously defined, and n is an integer from 1 to 6, or (2) an alcohol of formula $R^2OH$ to produce an alcoholysis product of formula VII:

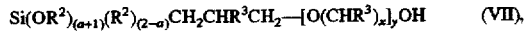

wherein $R^2$, $R^3$, a, x and y are as previously defined.

The above objects are also accomplished with a process comprising stages (A) and (B) above and further comprising:

(D) solvolyzing the organosilane ester of formula IV with either:

(1) water to produce a hydrolysis product of formula VI:

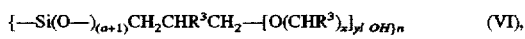 (VI), wherein $R^2$, $R^3$, x and y are as previously defined,
a is 0, 1 or 2, and
n is an integer from 1 to 6, or (2) an alcohol of formula $R^2OH$ to produce an alcoholysis product of formula VII:

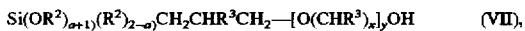 (VII), wherein $R^2$, $R^3$, x and y are as previously defined, and
a is 0, 1 or 2.

The above objects are also accomplished with a cyclic organosilane ester of formula IV:

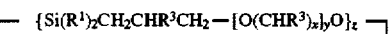 (IV)

where each $R^1$ is, independently, a hydrolyzable radical or $R^2$, $R^2$ is an organic radical bonded by a carbon atom, $R^3$ is hydrogen or a methyl radical, x is an integer from 2 to 6, y is 0 or an integer or fraction up to 60 and z is an integer from 1 to 6.

The above objects are also accomplished with a organyloxyorganylsilane ester of formula V:

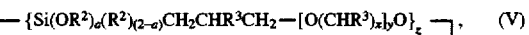 (V)

where each $R^1$ is, independently, a hydrolyzable radical or $R^2$, $R^2$ is an organic radical bonded by a carbon atom, $R^3$ is hydrogen or a methyl radical, x is an integer from 2 to 6, y is 0 or an integer or fraction up to 60, z is an integer from 1 to 6 and a is 1 or 2.

The above objects are also accomplished with the hydrolysis product of the cyclic organosilane ester IV or of the cyclic organylorganosilane ester V having formula VI:

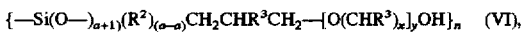 (VI), where $R^2$ is an organic radical bonded by a carbon atom, $R^3$ is hydrogen or a methyl radical, a is 0, 1 or 2, x is an integer from 2 to 6, y is 0 or an integer or fraction up to 60 and n is an integer from 1 to 6.

The above objects are also accomplished with the alcoholysis products of the cyclic organosilane ester IV or of the cyclic organylorganosilane ester V having formula VII:

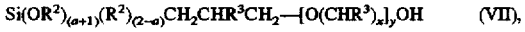 (VII), where $R^2$ is an organic radical bonded by a carbon atom, $R^3$ is hydrogen or a methyl radical, a is 0, 1 or 2, x is an integer from 2 to 6 and y is 0 or an integer or fraction up to 60.

The above objects are also accomplished with a composition containing:

(a) a compound of formula III, IV, V, VI or VII; and (b) a material selected from the group consisting of a polymer, a material containing a polyoxyalkylene group, a metal substrate, a mineral substrate and asphalt.

A more complete appreciation of the invention and many of the attendant advantages thereof will be readily obtained as the same becomes better understood by reference to the following detailed description.

DETAILED DESCRIPTION OF THE INVENTION

Stage (A)

The starting materials for stage (A) are the hydridosilane of formula I and the allyl compound of formula II which contains a hydroxyl group. The hydridosilane of formula I contains a hydrolyzable radical, X. The term "hydrolyzable radical" as used herein refers to a radical that may be substituted with —OH in a reaction with water. X is preferably a halide radical or an alkoxy radical. Preferably, the halide radical is fluorine, chlorine, bromine or iodine, more preferably chlorine or bromine and most preferably chlorine. The alkoxy group may have 1 to 10 carbon atoms, preferably 1 to 6, more preferably 1 to 4 and most preferably 1 or 2 carbon atoms. These carbon number ranges include all specific carbon numbers and subranges therebetween. The alkyl moiety of the alkoxy radical may have any structure, such as linear, branched or cyclic. X is preferably a halide radical.

Hydridosilane I contains two $R^1$ radicals. Each $R^1$ is, independently, a hydrolyzable radical or an $R^2$ radical. Preferable hydrolyzable radicals are the same as described for X above. $R^2$ is an organic radical bonded to the silicon atom by a carbon atom. Preferably, $R^2$ is a hydrocarbon radical, more preferably a $C_1-C_{14}$ hydrocarbon radical and most preferably a $C_1-C_{10}$ hydrocarbon radical. These carbon number ranges include all carbon numbers and subranges therebetween. The term "hydrocarbon radical" as used herein includes any hydrocarbon radical, such as alkyl, alkenyl, alkynyl, aryl, aralkyl, and alkaryl radicals. Preferably, the hydrocarbon radical is incapable of participating in any undesired side reaction in the invention process. An alkyl or phenyl radical is preferred. An alkyl radical is particularly preferred. A $C_1-C_4$ alkyl radical is particularly preferred. The term "alkyl radical" as used herein includes radicals having any structure, such as linear, branched and cyclic. Linear and branched alkyl radicals are preferred. Preferable examples of hydrocarbon radicals include methyl, ethyl, propyl, butyl (such as n-butyl and iso-butyl), pentyl, hexyl, cyclohexyl and phenyl radicals.

Accordingly, compound I may be a halosilane or an alkoxysilane, with a halosilane, particularly a chlorosilane, being preferred. Hydridosilane I reacts as a bifunctional molecule and must therefore also contain at least one hydrolyzable radical, X, in addition to the hydrogen atom, but may contain 2 or 3 hydrolyzable radicals when one or both $R^1$ groups are hydrolyzable radicals. Alternatively, hydridosilane I may contain 1 or 2 organic radicals bonded to the silicon atom by a carbon atom, i.e., $R^2$ radicals. Suitable hydridosilanes of formula I include trichlorosilane, methyldichlorosilane, ethyldichlorosilane, n-butyldichlorosilane, isobutyldichlorosilane, phenyldichlorosilane, cyclohexyldichlorosilane, dimethylchlorosilane, dimethylbromosilane and di-n-butylchlorosilane.

The allyl compound of formula II containing a hydroxyl group may be allyl alcohol or methalyl alcohol or a derivative of allyl alcohol or methalyl alcohol. Preferably, II is a derivative of allyl alcohol or methalyl alcohol. Suitable allyl compounds II may be prepared by the reaction of allyl alcohol or methalyl alcohol with one or more alkylene oxides, in particular with 1,2-propylene oxide and/or ethylene oxide. This reaction may produce a mixture of compounds of formula II because the oxyalkylation reaction may lead to a random molecular weight distribution. Accordingly, the variable y may be 0 or an integer or fractional value between 0 and 60. Preferably, y is 1 or an integer or fraction from 1 up to 60. More preferably, y is an integer or fraction from 1 to 10. These values for y explicitly include all specific values and subranges therebetween. A mixture of homologs of formula II may be separated by distillation. Alternatively, a mixture of compounds of formula II may be used in stage (A). In this case, the variable y may be a fraction as discussed above. Allyl compounds II may also be prepared by one-sided etherification of glycols or polyalkylene glycols, for example by the Williamson synthesis.

In formula II, x may be an integer from 2 to 6. This range for x includes all specific values and subranges therebetween, including 3, 4 and 5. Each $R^3$ in formula II may be, independently, hydrogen or a methyl radical. The $R^3$ in the $(CHR^3)_x$ group is preferably hydrogen when x is 4 to 6. Like the silane of formula I, II reacts as a bifunctional compound. Non-limiting examples allyl compounds II include allyl and methallyl alcohol, ethylene glycol monoallyl ether, ethylene glycol monomethallyl ether, 1,2-propylene glycol monomethallyl ether as an isomer mixture, 1,3-propylene glycol monoallyl ether, 1,4-butanediol monomethallyl ether, 1,6-hexanediol monoallyl ether, diethylene glycol monoallyl ether, di-1,4-butylene glycol monomethallyl ether, triethylene glycol monoallyl ether, tri-1,4-butylene glycol monomethallyl ether, tri-1,2-propylene glycol monoallyl ether as an isomer mixture, tetraethylene glycol monomethallyl ether, tetra-1,4-butylene glycol monoallyl ether and polyethylene glycol monoallyl ether having average molecular weights of 600 to 1200.

In this stage of the process, the two bifunctional compounds I and II react to produce the open-chain organosilane ester of formula III. A condensation reaction occurs between the hydroxyl group of the allyl compound II and the hydrolyzable radical X of hydridosilane I, which produces the olefinically unsaturated open-chain organohydridosilane ester of formula III.

If a halogen-containing hydridosilane I is used, molar amounts of hydrogen halide may be liberated during the condensation reaction. The hydridosilane I and the allyl compound II may be used in approximately stoichiometric amounts if a basic agent which neutralizes the resulting hydrogen halide in anhydrous form is added. Suitable basic agents include basic ion exchangers and tertiary amines, such as triethylamine, tri-n-butylamine, tertiary dodecylamine (i.e., tridodecylamine) and pyridine. The reaction may also be conducted in the absence of a basic agent by "boiling off" the hydrogen halide, i.e. driving it out of the boiling reaction mixture with the vapors of low-boiling component(s). In this case, it is preferable to use hydridosilane I in a stoichiometric excess, for example in 2 to 20 times the stoichiometric amount.

The condensation reaction may be carried out within a wide temperature range. The reaction temperature is preferably 0° to 80° C. when a basic substance is used to neutralize the hydrogen halide. The reaction temperature is preferably the boiling point of the system when the hydrogen halide is "boiled of", i.e., no basic agent is used. Compounds I and II may be reacted with one another in undiluted form. Alternatively, the reaction may be conducted in an inert solvent. More preferably, the inert solvent is a hydrocarbon having a boiling point of 80° to 150° C. Most preferably, the hydrocarbon has a boiling point of 95° to 120° C. Examples of inert solvents include ortho-, meta- and para-xylene, toluene and methylcyclohexane. Toluene and methylcyclohexane are preferred. The reaction time is preferably sufficient to produce ester III. Preferably, the reaction time is 15 minutes to 3 hours, more preferably 15 minutes to 2 hours and most preferably 20 minutes to 1 hour. The reaction is preferably carried out at atmospheric pressure.

After completion of the condensation reaction, the reaction mixture may be worked up by distillation, if appropriate, after separating off the basic agent which has neutralized the hydrogen halide, where any excess hydridosilane I preferably distills off first. However, the hydridosilane ester III is preferably of such high purity that it may be used directly in crude form without further purification.

Stage (B)

In this stage of the invention process, the olefinically unsaturated open-chain organohydridosilane ester of formula III is converted to cyclic organosilane ester IV. Since the reaction preferably proceeds intramolecularly, the hydrosilylation produces the cyclic organosilane ester IV. In the case of short chains (for example y=0) which provide a 5- or 6-membered ring product, the desired intramolecular hydrosilylation is the preferred reaction pathway. With longer chains (for example y>2), cyclic organosilane esters IV in which z>1 may be formed. Preferably, z is an integer from 1 to 6, more preferably from 1 to 3 and most preferably 1. The reaction conditions are preferably those which substantially avoid the formation of polymers.

The hydrosilylation reaction is preferably conducted in an inert solvent which serves as a diluent. Preferably, the inert solvent is a hydrocarbon. More preferably, the inert solvent is a hydrocarbon having a boiling point of 80° to 150° C. Most preferably, the hydrocarbon has a boiling point of 95° to 120° C. Examples of inert solvents include ortho-, meta- and para-xylene, toluene and methylcyclohexane. Toluene and methylcyclohexane are preferred. The inert solvent may already be present in part from the preceding condensation reaction of stage (A).

The reaction may be carried out in the presence of a hydrosilylation catalyst, preferably a catalytically active amount of a platinum compound. Preferably, the platinum compound is a platinum(II) derivative. Examples of platinum catalysts include platinum(II) acetate, platinum(II) acetylacetonate and hexachloroplatinic(II) acid and complexes thereof with divinyltetramethyl-disiloxane or with ketones. The platinum compound is preferably used in amounts corresponding to $10^{-3}$ to $10^{-6}$ mol of platinum per mole of open-chain silane ester III. The hydrosilylation reaction of stage (B) is preferably carried out at temperatures above 45° C., more preferably between 60° and 130° C. The reaction is preferably carried out at the boiling point of the inert solvent. Atmospheric pressure is preferred. Preferably, the open-chain silane ester III is added gradually to the boiling solution of the platinum catalyst in the inert solvent. A preferred addition time is 15 minutes to 2 hours, more preferably 20 minutes to 1.5 hours and most preferably 30 minutes to 1 hour. As compound III is added any excess hydridosilane I preferably distills off spontaneously. The reaction mixture may be heated after the addition, preferably for 30 minutes to 1.5 hours. Surprisingly, conducting the reaction in this fashion promotes the desired intramolecular cyclizing hydrosilylation reaction and avoids substantial formation of polymeric substances.

The cyclic organosilane ester IV may be isolated by distillation under reduced pressure, after the low-boiling components of the reaction mixture are removed. High molecular weight cyclic silanes of formula IV may not be amenable to purification by distillation. However, ester IV may also be used in crude form, as described below, or can be reacted further.

Stage (C)

If a hydridosilane I containing more than one halogen radical, i.e., at least one $R^1$ is a halogen radical, is used as the starting material in stage (A), then the cyclic organosilane ester IV produced in stage (B) will still contain at least one hydrolyzable halogen radical. This compound may be used directly in stage (D), as described below. Alternatively, an ester IV containing at least one hydrolyzable halogen radical may be reacted with a stoichiometric amount of an alcohol of the formula $R^2OH$. The $R^2$ group of the alcohol is preferably an organic radical. This radical is preferably bonded to the oxygen atom by a carbon atom. The preferred embodiments for $R^2$ are discussed above. An $R^2$ group in formula I may be the same or different from the $R^2$ group of the alcohol formula $R^2OH$, i.e., the $R^2$ groups are independently selected. More than one alcohol of formula $R^2OH$ may be used in the this stage of the process.

In this reaction, the hydrolyzable halogen radicals are replaced by an —$OR^2$ group to produce the organyloxyorganosilane ester of formula V. In formula V, the variable a may be 1 or 2. When one $R^1$ group in formula IV is a hydrolyzable halogen radicals and the other $R^1$ is a $R^2$ radical, compound V will contain one $OR^2$ radical and one $R^2$ radical. In this case, a is 1. When both $R^1$ groups in formula IV are hydrolyzable halogens, compound V will contain two $OR^2$ radicals and no $R^2$ radical. Accordingly, a is 2 in this case. Like organosilane ester IV, compound V is also sensitive to solvolysis with opening of the ring.

As in the condensation reaction of stage (A), a basic agent may be added in order to neutralize the resulting hydrogen halide in anhydrous form. The basic agents described above are suitable for this purpose. Alternatively, the condensation reaction may be conducted in the absence of a basic agent. In this case, the alcohol $R^2OH$ is preferably used in a stoichiometric excess and the hydrogen halide produced is "boiled off", preferably in the presence of a solvent. A preferred reaction time is 30 minutes to 2 hours. The reaction temperatures may be the same as stage (A) as described above. The condensation reaction of stage (C) is preferably carried out at atmospheric pressure.

Stage (D)

In this stage of the invention process, the organosilane ester IV from stage (B) or the organyloxyorganosilane ester V from stage (C) is solvolyzed. Solvolysis of IV or V with water produces the corresponding hydrolysis product VI. Alternatively, IV or V may be solvolyzed with an alcohol of formula $R^2OH$ to produce the corresponding alcoholysis product of formula VII. It is not important for the nature of the solvolysis products whether z is 1 or z is greater than 1 in the cyclic silane esters IV and V.

When the cyclic silane esters IV or V contain substituents $R^1$ which are organic radicals bonded by a carbon atom, i.e., —$R^2$, these substituents are retained during the solvolysis reaction. When the cyclic ester IV from stage (B) is solvolyzed, the resulting solvolysis product VI or VII may contain zero, one or two $R^2$ groups and the variable a may therefore be 0, 1 or 2. If product VI or VII contains no $R^2$ groups, then a is 2. If the solvolysis product contains one $R^2$ group, then a is 1. When VI or VII has two $R^2$ groups, a is 0.

When the cyclic ester V from stage (C) is solvolyzed, the solvolysis product VI or VII may contain zero or one—$R^2$ radicals bonded to the silicon atom and the variable a may therefore be 1 or 2. If product VI or VII contains no $R^2$ group, then a is 2. When VI or VII contains one $R^2$ group bonded to silicon, a is 1.

If the cyclic silane ester IV or V contains hydrolyzable radicals as substituent $R^1$, silanol groups are initially formed therefrom during the hydrolysis. A terminal alcoholic hydroxyl group and a silanol group are also formed as a result of the opening of the ring. Since the silanol groups tend to undergo condensation to form siloxane structures, e.g., 13 Si—O—Si—, the hydrolysis products VI are of higher molecular weight, depending on the value of n. Variable n may be an integer from 1 to 6. In a preferred embodiment, n is an integer from 1 to 4. In another preferred embodiment, n is an integer from 2 to 6. In still another preferred embodiment, n is an integer from 2 to 4. These ranges for n include all specific values and subranges therebetween. In formula VI, the siloxane structures are indicated by the symbol —Si(O)—. The type of condensation products formed depends on the substitution of the silicon atom. If the silane esters IV and V contain no hydrolyzable radicals in addition to the cyclic ester grouping, disiloxanes are formed. If one hydrolyzable radical is also present, compounds may be formed having siloxane structures in which three or more Si—O units form a ring with 6, 8, 10 and so on ring members and an alternating sequence of Si and 0 atoms or open linear chains, with the other valencies of the Si atoms being satisfied by organic radicals. Preferred cyclic siloxanes are those having 3 to 8 silicon atoms in the ring. If the silane esters IV and V also contain two hydrolyzable radicals, then crosslinked siloxane-rich structures which have organic radicals bonded covalently to silicon and are highly viscous liquids or have a tough, rubbery consistency may be formed during the hydrolysis. Preferably, the hydrolysis product of formula VI is predominantly a disiloxane, a cyclic siloxane having 3 to 8 silicon atoms in the ring, a linear polysiloxane or a crosslinked polysiloxane.

The hydrolysis may be carried out by gradually introducing the silane ester IV or V into excess water. It is preferable to use the silane ester as a solution in an inert, water-immiscible solvent, and to ensure thorough mixing of the aqueous and organic phase. Suitable solvents include the inert solvents described above. The reaction may be carried out at room temperature. Alternatively, the reaction mixture may be heated. Heating at the reflux temperature of the reaction mixture is preferred. The reaction time is preferably an amount of time sufficient to complete the hydrolysis reaction. A preferred reaction time is 30 minutes to 3 hours, more preferably 30 minutes to 2 hours and most preferably 45 minutes to 1.5 hours. If the silane ester IV contains hydrolyzable halogens, a basic agent may be added to neutralize the hydrogen halide. Suitable such basic agents are the agents described above for this purpose. Also, alkali metal carbonates and bicarbonates may be used. The alkali metal carbonates and bicarbonates are preferred. Alternatively, the hydrogen halide may also be removed from the reaction mixture by boiling off. When the hydrolysis reaction is complete, the hydrolysate may be taken up in an inert, water-immiscible solvent. The solvent may be evaporated and the hydrolysate may be obtained as the resulting residue.

The alcoholysis in stage (D) may be regarded as the completion of the alcoholysis reaction which leads to the organyloxyorganosilane ester V in optional stage (C), when the cyclic organosilane esters IV contains halogen radicals as substituents $R^1$. The reaction in stage (C) is possible because exchange of the halogen atoms for —$OR^2$ radicals takes place more easily than opening of the ring by alcoholysis. Those organosilane esters IV which contain no halogen atoms and therefore cannot form organyloxyorganosilane esters V are of course also susceptible to alcoholysis in stage (D). Organyloxy radicals, such as alkoxy radicals, present as substituent $R^1$ in the cyclic silane esters IV and V are retained during the alcoholysis. Halogen atoms are replaced by alkoxy radicals during alcoholysis. A terminal alcoholic hydroxyl group and, on the silicon atom, an alkoxy group are formed during opening of the ring. The omega-hydroxyorganyl-alkoxysilanes are represented in monomeric form by the general formula VII. However, they may also undergo intermolecular condensation to give open-chain oligomers or polymers. This condensation reaction may be prevented or inhibited by stabilizing agents. Suitable stabilizing agents include the alcohols of the formula $R^2OH$ in amounts of up to 35% by weight. The preferred embodiments for the $R^2$ group are discussed above. Alcohols having 1 to 4 carbon atoms are particularly preferred (such as methanol and ethanol). Another preferred stabilizing agent is a tertiary amine, such as a trialkylamine having up to 48 carbon atoms (e.g., tertiary dodecylamine). The tertiary amine is preferably used in small amounts. A preferred amount is 0.02 to 0.3% by weight, more preferably 0.5 to 0.2% by weight and most preferably 0.75 to 0.15% by weight. A particularly preferred amount of the tertiary amine is 0.1% by weight. A mixture of the alcohol and the tertiary amine may be used as a stabilizing agent. The oligomeric or polymeric esters may be converted back to the monomeric form by treatment with an alcohol.

The alcoholysis may be accomplished by gradually adding silane ester IV or V to the alcohol. Ester IV or V may be dissolved in an inert solvent before addition to the alcohol. The reverse sequence of addition is also possible, i.e., adding the alcohol to ester IV or V. The reaction may be carried out at room temperature. Alternatively, the reaction mixture may be heated, preferably from room temperature up to the boiling point of the solution at reflux. The reaction is preferably conducted for a time sufficient to complete the reaction. A preferred reaction time is 10 minutes to 2 hours, more preferably 15 minutes to 1 hour. As with the hydrolysis, a basic agent which neutralizes any hydrogen halide produced may be added to the reaction mixture when the silane ester IV also contains hydrolyzable halogen, or the hydrogen halide can be removed by boiling off. An alkali metal salt of the alcohol may be used, such as a sodium or potassium salt. A sodium salt is preferred.

If the silane ester IV contains one or two hydrolyzable halogen radicals, the condensation reaction in which hydrogen halide is formed and the halogen is replaced by an organyloxy radical (i.e., the same reaction as stage C) and the solvolysis resulting in ring opening compete with one another. The condensation reaction is kinetically preferred. As a result, it is possible to prepare cyclic organyloxyorganosilane esters V with stoichiometric amounts (i.e. 1 or 2 mol) of alcohol, as described above under stage C. However, these products are sensitive to solvolysis. Therefore, if a cyclic organyloxyorganosilane ester V is subjected to hydrolysis or alcoholysis, the same product as is formed by reaction of cyclic organosilane esters IV containing hydrolyzable halogen with excess (i.e. in excess of 1 or 2 mol) amounts of water or alcohol is obtained. However, in some cases it is appropriate first to convert cyclic organylsilane ester IV containing hydrolyzable halogen into organyloxyorganylsilane ester V in stage C, and then to solvolyze V in stage D. This applies, for example, if the solvolysis takes place when the process products are used on substrates which are sensitive to hydrogen halide and agents which bind hydrogen halide are detrimental or even run counter to the intended use.

Use of the Process Products

The invention silanes III, IV, and V and the solvolysis products VI and VII may be used as crosslinking agents and/or adhesives, particularly with epoxy resins, materials containing polyoxyalkylene groups (such as LYCRA and HYTREL), polyurethanes and polymers containing ester groups. When applied as a solution, compounds III–VII produce firm bonds between two identical or different materials described above. Compounds III–VII may also be used to bond and/or crosslink polymers and metallic or mineral substrates together. These substrates may be flat or finely divided, i.e., fillers. Suitable fillers include alumina minerals, silicate minerals, silicic acid in its various forms, calcium carbonate, enamels, all forms of glass (such as glass fibers, glass beads and cellophane), carbon blacks and metal powders. The invention compounds III–VII may also be used as phase mediators, for example between asphalt polymers, such as polyalkylenes or polyvinyl chloride and silicones.

Accordingly, the present invention includes a composition containing (a) compound III, IV, V, VI or VII and (b) a material selected from the group consisting of a polymer, a material containing a polyoxyalkylene group, a metal substrate, a mineral substrate and asphalt. It is to be understood that this composition may contain (a) and material (b), reaction products thereof or both. A preferable reaction product is one obtained by crosslinking (a) with material (b). Another preferable reaction product is one obtained by adhering (a) to (b). The composition may be obtained by contacting (a) and (b) using techniques well-known to those of skill in the art. The invention composition may contain more than one of compounds III–VI. This composition may also contain more than one material (b), preferably two different types of such materials.

The solvolysis products VI and VII which contain free hydroxyl groups may also be used to modifying an organic polymer material that contains at least one ester group by transesterification. In this reaction, transesterification catalysts are preferably used. If these materials modified by transesterification are then treated with water or steam, crosslinking may occur at the silane groupings introduced. Suitable base polymers containing at least one ester group include homo- or copolymers of acrylic acid esters, methacrylic acid esters and maleic acid esters.

Having generally described this invention, a further understanding can be obtained by reference to certain specific examples which are provided herein for purposes of illustration only and are not intended to be limiting unless otherwise specified.

EXAMPLES

Example 1

(a) 1-Sila-2-oxa-1-chloro-1,4-dimethylcyclopentane 760 g (6.6 mol) of methylhydridodichlorosilane were initially introduced into a 2 L stirred reactor with temperature regulation with temperature measurement in the liquid phase, a metering funnel which extends into the liquid phase with its discharge and a reflux condenser operating at −80° C., with a line for removing gaseous hydrogen chloride, and were heated to the boiling point. 216 g (3 mol) of methallyl alcohol were metered in over a period of 30 minutes and the 3 mol of hydrogen chloride formed were boiled off completely in the course of 30 minutes. The resulting solution of about 450 g (3 mol) of methylhydridomethallyloxychlorosilane in about 400 g of methylhydridodichlorosilane was metered in the course of 45 minutes into another 2 L stirred reactor which was provided with a packed column with 9 trays under a distillation head, in which 1 L of boiling toluene containing 1 mL of an N/100 solution of hexachloroplatinic(II) acid in acetone was initially introduced. During this procedure, the excess methylhydridodichlorosilane distilled off spontaneously. The reaction mixture was subsequently stirred at the boiling point for 1 hour. A solution of about 440 g of the target product in toluene was formed.

(b) 1-Sila-2-oxa-1-sec-butoxy-1,4-dimethylcyclopentane

The solution, prepared in stage (a), of the target product in toluene was initially introduced into a 4 L stirred reactor with temperature regulation and a reflux condenser and was heated to 70° C. A solution of 225 g (3 mol) of sec-butanol and 245 g (3.1 mol) of pyridine in 800 ml of toluene was added dropwise in the course of one hour. Pyridine hydrochloride precipitated out during this procedure. The mixture was stirred for a further hour and then cooled to 0° C. The pyridine hydrochloride was filtered off and washed 4 times with 200 ml of ice-cold toluene each time. Distillation of the combined toluene solutions gave 408 g (72% of theory) of the target product of boiling point 63° to 68° C. under 2 mbar.

(c) 3-Hydroxyisobutyl-methylsiloxane oligomer as a hydrolysate

A solution, prepared according to stage (a), of the target product in toluene was introduced into a suspension of 260 g (3.1 mol) of sodium bicarbonate in 600 mL of water at room temperature in the course of one hour, while stirring and cooling. Two phases formed, with evolution of gas. The lower phase comprised an approximately 30% strength sodium chloride solution. The upper phase comprised the target product as a solution in toluene. After the toluene had been stripped off in vacuo, 378 g of a viscous oil remained as the target product.

Example 2

(a) 1-Sila-2,5-dioxa-1-chloro-1,3(4),7-trimethylcyclooctane

Analogously to Example 1 (a), 195 g (1.5 mol) of a mixture of 1-methallyl-2-propanol and 2-methallyl-1-propanol (prepared from methallyl chloride and 1,2-propanediol by the Williamson synthesis in a manner known per se) were esterified with 380 g (3.3 mol) of boiling methylhydridodichlorosilane. The solution which comprised the resulting monoester mixture was subjected to cyclizing hydrosilylation analogously to the procedure described in Example 1 (a) to give the target product in toluene.

(b) 1-Sila-2,5-dioxa-1-ethoxy-1,3(4),7-trimethylcyclooctane

Analogously to Example 1(b), a solution of 70 g (1.5 mol) of ethanol in 126 g (1.6 mol) of pyridine was added to the solution of the target product of stage 2(a) at 50° C. The subsequent procedure was as in Example 1(b). 223 g (68% of theory) of target product of boiling point 137° to 148° C./1 mbar were obtained.

(c) 3-(2- or 1-Hydroxy-1- or 2-propoxy)-isobutyl-methylsiloxane oligomer as a hydrolysis product The product prepared in stage 2(a) was metered into a suspension of 130 g (1.55 mol) of sodium bicarbonate in 300 ml of water at room temperature in the course of one hour, while stirring and cooling. Two phases formed, with the evolution of gas. The upper phase was dried with sodium sulfate. After the toluene had been stripped off in vacuo, 252 g of the target product remained as a pale yellow viscous oil.

Example 3

(a) 1-Sila-2-oxa-1,1-dichlorocyclopentane 1110 g (8.2 mol) of trichlorosilane were initially introduced into a 2 L stirred reactor with temperature regulation with temperature measurement in the liquid phase, a metering funnel extending into the liquid phase with its discharge and a reflux condenser operating at −80° C., with a line for removing gaseous hydrogen chloride, and were heated to the boiling point. 116 g (2 mol) of allyl alcohol were metered in over a period of 20 minutes, and the hydrogen chloride formed was boiled off completely in the course of a further 20 minutes. The resulting solution of about 310 g of hydridoallyloxydichlorosilane in about 840 g of trichlorosilane was metered in the course of 45 minutes into a 2 L stirred reactor which was provided with a packed column with 9 trays under a distillation head with a liquid divider into which 500 ml of boiling methylcyclohexane which contained 0.5 ml of an N/100 solution of hexachloroplatinic(II) acid in acetone had been initially introduced. The excess trichlorosilane (about 840 g) distilled off spontaneously during this procedure. The reaction mixture was subsequently stirred for one hour. A solution of about 300 g of the target product in methylcyclohexane resulted.

(b) 3-Hydroxypropyltriethoxysilane as an ethanolysis product 184 g (4 mol) of ethanol were metered at 58° C. in the course of 20 minutes into the solution, prepared in stage 3(a), of the target product, which was in a 2 L stirred reactor with a reflux condenser operating at −80° C., a line for removing hydrogen chloride, temperature regulation in the liquid phase of the reactor and a metering funnel dipping into the liquid phase with its discharge. The mixture was heated to the boiling point, and as a result the hydrogen chloride formed (about 2 mol) was boiled off. The reaction mixture was cooled and passed into a solution of 136 g (2 mol) of sodium ethanolate in ethanol in the course of 30 minutes, sodium chloride precipitating out. The boiling solution was subsequently neutralized dropwise against pH paper with ethanolic sodium ethanolate solution and then cooled to 0° C. The sodium chloride was filtered off and washed 4 times with 50 ml of ice-cold methylcyclohexane each time. The crude solution of the target product was filtered over active charcoal. After addition of 0.5 ml of tertiary dodecylamine (tridodecylamine) as a stabilizing agent, excess ethanol and methylcyclohexane were stripped off in vacuo, a product temperature of 40° C. not being exceeded. 392 g of the target product (88% of theory) remained as a pale yellow viscous oil. The product was additionally stabilized by addition of 47 g of ethanol.

Without addition of 0.4 g of tertiary dodecylamine, a product crosslinked in a rubber-like manner, which liquefied again on heating with methanol or ethanol, was obtained during working up of the crude product by distillation.

Example 4

(a) 1-Sila-2,5,8,11,14-pentaoxa-1,1-dichlorocycloheptadecane

Analogously to Example 3(a), 235 g (1 mol) of tetraethylene glycol monoallyl ether (prepared from allyl chloride and tetraethylene glycol by the Williamson synthesis in a manner known per se) were reacted with 814 g (6 mol) of trichlorosilane in the course of 30 minutes to give the corresponding hydridodichlorosilane monoester, which was then subjected to cyclizing hydrosilylation to give about 330 g of the target product, dissolved in methylcyclohexane.

(b) 3-(2-Hydroxy-omega-tetraethoxy)propyltrimethoxysilane as a methanolysis product The solution, prepared in stage (a), of the target product was stirred, at room temperature and while cooling, into a 30% strength by weight solution of sodium methylate in methanol which had been initially introduced into a 2 L stirred reactor, sodium chloride precipitating out. Thereafter, the reaction mixture was subsequently neutralized dropwise against pH paper with methanolic sodium methylate solution, while boiling gently. After working up analogously to Example 3(b), 0.3 g of tertiary dodecylamine was added to the solution of the target product, and methanol and methylcyclohexane were stripped off in vacuo, a product temperature of 40° C. not being exceeded. 312 g (87% of theory) of the target product remained as a pale yellow viscous oil, which was additionally stabilized by addition of 15 g of methanol.

Example 5

(a) Cyclization product from 1,4-tributylene glycol monoallyl ether and hydridodimethyidichlorosilane 138 g (0.5 mol) of 1,4-tributylene glycol monoallyl ether (prepared from allyl chloride and tributylene glycol by the Williamson synthesis in a manner known per se) were liquefied by means of 100 ml of methylcyclohexane, and the solution was reacted with 345 g (3 mol) of methyldichlorosilane analogously to Example 3(a) to give the corresponding hydridomethylchlorosilane ester, which was subsequently subjected to cyclizing hydrosilylation to give about 170 g of the target product, dissolved in methylcyclohexane.

(b) 3-(4-Hydroxy-omega-tri-1,4-butylenoxy)-propylmethylsifoxane oligomer as a hydrolysis product The solution, prepared in stage (a), of the cyclization product was hydrolyzed with 52 g of sodium bicarbonate in 200 ml of water analogously to Example 1 (c), and the reaction was brought to completion by heating at the boiling point for 2 hours. After working up, 160 g (95% of theory) of the target product remained as a pale yellow oil which slowly solidified at room temperature.

Example 6

(a) Cyclization product from polyethylene glycol monoallyl ether and trichlorosilane 94 g (0.1 mol) of polyethylene glycol monoallyl ether (average molecular weight 940, average degree of polymerization about 20; prepared by ethoxylation of ethylene glycol monoallyl ether in a manner known per se) were liquefied by means of 100 mL of toluene, and the solution was reacted with 270 g (2 mol) of trichlorosilane analogously to Example 3(a) to give the corresponding hydridodichlorosilane ester, which was subsequently hydrosilylated with 300 ml of toluene, which contained 0.7 ml of catalyst, to give about 100 g of the target product, dissolved in toluene.

(b) Polyethylene glycol mono-(3-trimethoxysilyl)propyl ether as a methanolysis product The solution, prepared according to Example 6(a), of the target product was esterified with 5.4 g (0.1 mol) of sodium methylate in 50 ml of methanol analogously to Example 4(b). The sodium chloride which had precipitated out was filtered off and washed twice with 30 mL of ice-cold methanol each time. After addition of 0.1 mL of tertiary dodecylamine, the solution was freed from readily volatile substances in vacuo, the product temperature not exceeding 54° C. 98 g (92% of theory) of the target product remained as a pale yellow, highly viscous oil, which slowly solidified at room temperature. The Si content was 2.8%. The product could additionally be stabilized by addition of 2 g of methanol.

Obviously, numerous modifications and variations of the present invention are possible in light of the above teachings. It is therefore to be understood that within the scope of the appended claims, the invention may be practiced otherwise than as specifically described herein.

This application is based on German-patent application 196 28 588.7, filed Jul. 16, 1996, and incorporated herein by reference in its entirety.

What is claimed as new and desired to be secured by letters patent of the United States is:

1. A process for preparing a cyclic silane ester or a solvolysis product thereof, comprising:

(A) reacting a hydridosilane of the general formula I:

wherein X is a hydrolyzable radical, each $R^1$ is, independently, a hydrolyzable radical or $R^2$, and $R^2$ is an organic radical bonded by a carbon atom, with an allyl compound formula II:

wherein each $R^3$ is, independently, hydrogen or a methyl radical, x is an integer from 2 to 6, and y is 0 or an integer or fraction up to 60, to produce an organohydridosilane ester of formula III:

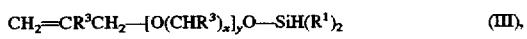

wherein $R^1$, $R^3$, x and y are as previously defined; and (B) intramolecularly hydrosilylating said ester of formula (III) to produce a cyclic organosilane ester of formula IV:

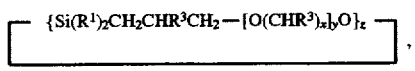

wherein $R^1$, $R^3$, x and y are as previously defined, and z is an integer from 1 to 6.

2. The process of claim 1, wherein said hydrolyzable radical is a halogen.

3. The process of claim 1, wherein said hydrolyzable radical is a halogen and $R^2$ is a $C_{1-C6}$ alkyl group.

4. The process of claim 1, wherein x is an integer from 1 to 4 and y is 0 or an integer or fraction up to 10.

5. The process of claim 1, wherein y is an integer from 1 to 5.

6. The process of claim 1, further comprising:

(C) reacting said cyclic ester of formula IV with an alcohol having the formula $R^2OH$ to produce a cyclic organyloxyorganosilane ester of formula V:

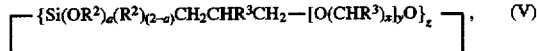

wherein at least one $R^1$ in formula IV is a halogen radical, $R^3$, x, y and z are as previously defined, each $R^2$ is, independently, as previously defined, and a is 1 or 2.

7. The process of claim 6, further comprising:

(D) solvolyzing said organyloxyorganosilane ester of formula V with either:

(1) water to produce a hydrolysis product of formula VI:

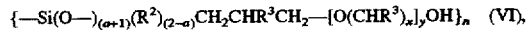

wherein $R^2$, $R^3$, a, x and y are as previously defined, and n is an integer from 1 to 6, or (2) an alcohol of formula $R^2OH$ to produce an alcoholysis product of formula VII:

  (VII)

wherein $R^2$, $R^3$, a, x and y are as previously defined.

8. The process of claim 7, wherein said solvolysis is hydrolysis with water and said hydrolysis product of formula VI is predominantly a disiloxane, a cyclic siloxane having 3 to 8 silicon atoms in the ring, a linear polysiloxane or a crosslinked polysiloxane.

9. The process of claim 7, wherein said solvolysis is alcoholysis and further comprising stabilizing said alcoholysis product of formula VII by adding a tertiary amine and/or an alcohol.

10. The process of claim 1, further comprising:
(D) solvolyzing said organosilane ester of formula IV with either:
(1) water to produce a hydrolysis product of formula VI:

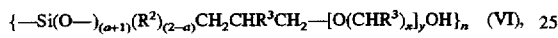 (VI), wherein $R^2$, $R^3$, x and y are as previously defined,
a is 0, 1 or 2, and
n is an integer from 1 to 6, or (2) an alcohol of formula $R^2OH$ to produce an alcoholysis product of formula VII:

 (VII), wherein $R^2$, $R^3$, x and y are as previously defined, and
a is 0, 1 or 2.

11. The process of claim 10, wherein said solvolysis is hydrolysis with water and said hydrolysis product of formula VI is predominantly a disiloxane, a cyclic siloxane having 3 to 8 silicon atoms in the ring, a linear polysiloxane or a crosslinked polysiloxane.

12. The process of claim 10, wherein said solvolysis is alcoholysis and further comprising stabilizing said alcoholysis product of formula VII by adding a tertiary amine and/or an alcohol.

13. A composition comprising:
(a) a cyclic organosilane ester of the formula IV produced by the process of claim 1, and
(b) a material selected from the group consisting of a polymer, a material containing a polyoxyalkylene group, a metal substrate, a mineral substrate and asphalt.

14. The cyclic organosilane ester of formula IV produced by the process of claim 1.

15. A composition comprising:
(a) a cyclic organosiloxane ester of the formula V produced by the process of claim 6, and
(b) a material selected from the group consisting of a polymer, a material containing a polyoxyalkylene group, a metal substrate, a mineral substrate and asphalt.

16. The cyclic organosilane ester of formula V produced by the process of claim 6.

17. A hydrolysis product of a cyclic organosilane ester having formula VI:

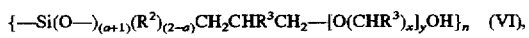 (VI), wherein each $R^2$ is, independently, an organic radical bonded by a carbon atom;

each $R^3$ is, independently, hydrogen or a methyl radical;

x is an integer from 2 to 6;

y is 0 or an integer or fraction up to to 60;

a is 0, 1 or 2; and n is 1 to 6.

18. A hydrolysis product of a cyclic organosilane ester having formula VI which is produced by the process of claim 7.

19. A hydrolysis product of a cyclic organosilane ester having formula VI which is produced by the process of claim 10.

20. An alcoholysis product of a cyclic silane ester having formula VII:

 (VII), wherein each $R^2$ is, independently, an organic radical bonded by a carbon atom;

each $R^3$ is, independently, hydrogen or a methyl radical;

x is an integer from 2 to 6;

y is 0 or an integer or fraction up to 60; and a is 0, 1 or 2.

21. An alcoholysis product of a cyclic silane ester having formula VII which is produced by the process of claim 7.

22. An alcoholysis product of a cyclic silane ester having formula VII which is produced by the process of claim 10.

23. A composition comprising:
(a) a hydrolysis product of a cyclic organosilane ester of the formula VI produced by the process of claim 7, and
(b) a material selected from the group consisting of a polymer, a material containing a polyoxyalkylene group, a metal substrate, a mineral substrate and asphalt.

24. A composition, prepared by aprocess comprising transesterifying a polymer containing at least one ester group with the hydrolysis product of claim 17.

25. A composition, prepared by a process comprising transesterifying a polymer containing at least one ester group with the alcoholysis product of claim 20.

26. A composition comprising a hydrolysis product of a cyclic organosilane ester of the formula VI produced by the process of claim 10, and
(b) a material selected from the group consisting of a polymer, a material containing a polyoxyalkylene group, a metal substrate, a mineral substrate and asphalt.

* * * * *